United States Patent [19]
Peszynski

[11] Patent Number: 5,602,718
[45] Date of Patent: Feb. 11, 1997

[54] THERMAL SINK FOR A TRANSDUCER ASSEMBLY

[75] Inventor: Michael Peszynski, Newburyport, Mass.

[73] Assignee: Hewlett-Packard Company, Palo Alto, Calif.

[21] Appl. No.: 536,412

[22] Filed: Sep. 29, 1995

[51] Int. Cl.⁶ .................................................. H05K 7/20
[52] U.S. Cl. .......................................... 361/704; 361/715
[58] Field of Search ..................................... 361/704–730

[56] References Cited

U.S. PATENT DOCUMENTS

| | | | |
|---|---|---|---|
| 4,763,225 | 8/1988 | Frenkel et al. | 361/709 |
| 4,935,864 | 6/1990 | Schmidt et al. | 361/719 |

Primary Examiner—Gregory D. Thompson
Attorney, Agent, or Firm—Pamela L. Kee

[57] ABSTRACT

Active thermal conduction of a transducer array at the distal end of an imaging probe maintains the temperature of the transducer array below a predetermined limit so as not to damage human body tissue. A thermally conductive rotor is connected between the back face of the transducer array and a stator that behaves as a heat sink. A dual ball bearing arrangement is placed near the rotor/stator interface to allow rotation of the transducer array while providing thermal conduction. An optional layer of oil may be placed between the rotor and the stator to promote heat transfer.

4 Claims, 3 Drawing Sheets

THERMAL SINK FOR A TRANSDUCER ASSEMBLY

FIELD OF THE INVENTION

The invention is directed toward ultrasound imaging and more specifically, to system for providing active thermal conduction of a transducer array at the distal end of an imaging probe, such as a transesophogeal endoscopic probe or a transthoracic probe.

BACKGROUND OF THE INVENTION

Echo ultrasound is an established technique in the area of medical imaging. Typically, an ultrasound imaging system has electronics for remote excitation of an ultrasound transducer array or probe to obtain cross-sectional images of the internal organs along a variety of planes.

The transducer array can be a linear array, a curved linear array or a phased array. The basic structure of each array includes a plurality of transducer elements which are arranged adjacent to one another along a surface. The sequence of exciting the transducers differs. In a linear array, the transducers are excited sequentially in a "tractor treading" pattern and form a rectangular image or "window". Typically, a multiplexor is used within the probe to effectuate the sequential excitation of the transducer elements. The multiplexor generates heat during the ultrasound procedure. The power used to excited the transducer elements also generates heat at the transducer array. A phased array system uses a non-sequential excitation of the transducer elements and the image resulting from a phased array transducer is typically a pie-shape. The phased array provides an image of the organ which may be blocked by dense tissue such as bone. For example, the phased array transducer produces an image which fans our from a point, typically the center of the array on the probe. The use of a phased array transducer enables a transthoracic probe to image the heart through various acoustic windows about the body. Heat is also generated at the transducer elements because of the power used to excite the elements.

Typically, the transmit frequency used in ultrasound imaging machines that generates satisfactory image clarity is in the range of 2–10 MHZ. When the aperture of the array is reduced, the frequency of the signal is typically increased (or wavelength reduced) to maintain the desired wavelength best suited to image an organ. However, when the frequency of the sound signal is increased, the signal becomes more quickly attenuated and the image penetration is reduced. One way to regain image penetration is to increase the power with which the signal is supplied to the transducer array. The increased power enables a smaller array to generate an image having the penetration of the larger lower frequency array. However, the increased power also generates an undesirable amount of heat at the transducer array. When using a transesophogeal imaging transducer, increased heat is especially problematic because the only place to dissipate the heat is within the esophagus. Since the temperature of a lens of a TEE probe cannot rise above 41° C. per the FDA limit, the increased power, and the concomitant increase in temperature, may create an unsafe condition for the patient.

A desirable system is one that maintains the temperature of the transducer array below a predetermined limit which will not cause damage to body tissue, while providing adequate power to image small features at appropriate depths.

SUMMARY OF THE INVENTION

Active thermal conduction of a transducer array at the distal end of an imaging probe maintains the temperature of the transducer array below a predetermined limit so as not to cause damage to body tissue. At the distal end of the imaging probe is a transducer array used for scanning a body. Attached to the back face of the transducer array is a rotor of thermally conductive material. A stator of thermally conductive material is positioned near the stator. There is a thin layer of oil between the rotor and the stator. A ball bearing preload screw fastens the rotor, the stator, and the transducer array together. A first ball bearing is placed near the interface between the rotor and the stator. A second ball bearing is placed near the stator and the ball bearing preload screw. During operation, the thin oil layer transfers heat from the rotor to the stator by virtue of lower temperatures and heat sinking capabilities of the stator.

DETAILED DESCRIPTION OF THE PREFERRED EMBODIMENTS

Figure 1:
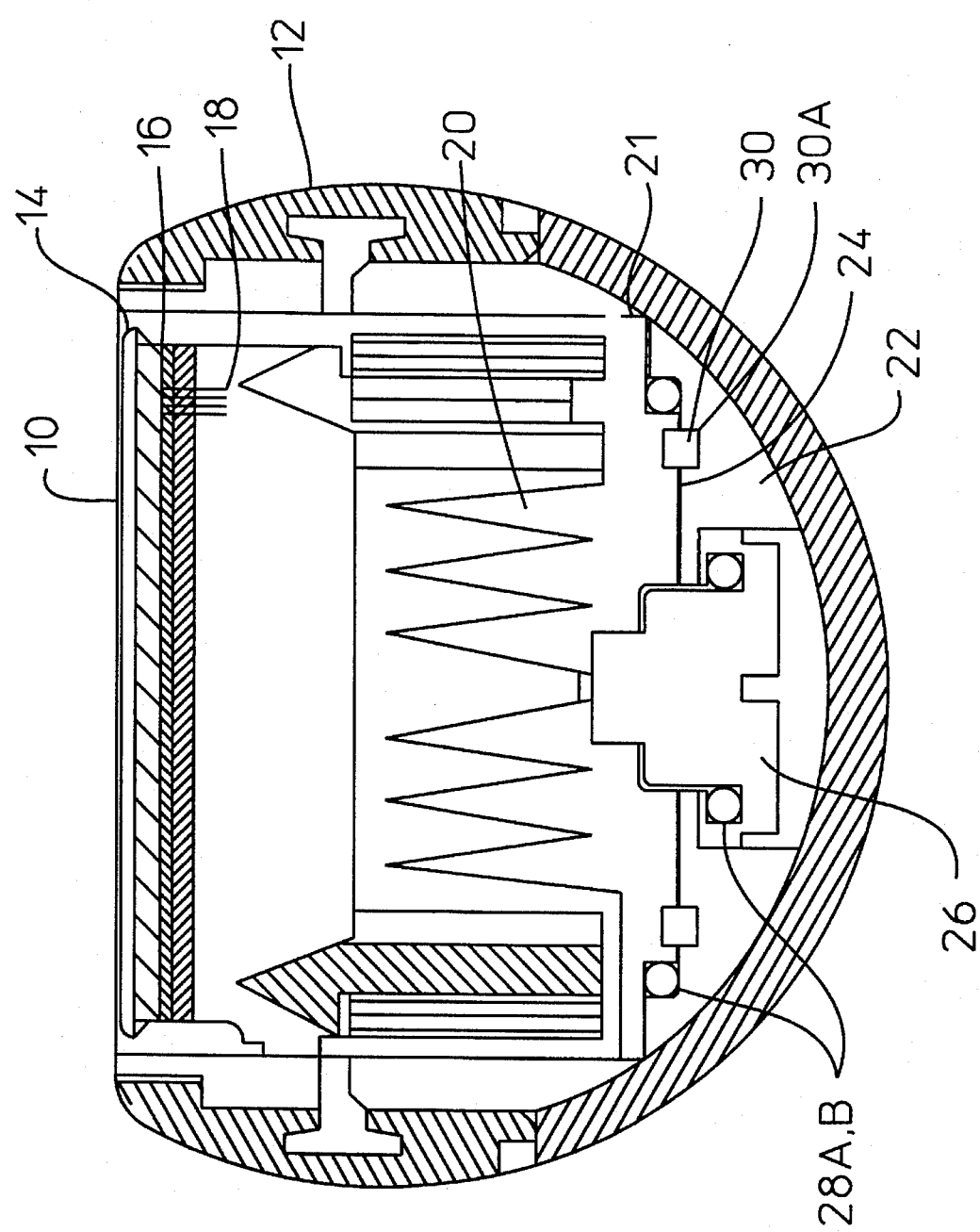
FIG. 1 illustrates a cooling system for a distal end of a probe housing.

FIG. 1 illustrates a cooling system for cooling a distal end of an imaging probe 2. An acoustic lens 10 is positioned at one end of a probe housing 12. An acoustic matching layer 14 is positioned adjacent to the acoustic lens 10. A resonator 16, such as a transducer array, is sandwiched between the acoustic matching layer 14 and an acoustic backing layer 18. The acoustic backing layer 18 is further attached to a backing heat sink 20 that is coupled to a rotor 21 of thermally conductive material. A fixed heat sink 22, such as a stator of thermally conductive material is positioned near the backing heat sink 20. There is a thermal coupling media 24, such as a thin oil layer, between the rotor and the stator. A ball bearing preload screw 26 fastens the rotor 21, the stator 22, and the resonator 16 together. A first ball bearing 28A is placed near the interface between the rotor 21 and the stator 22. A second ball bearing 28B is placed near the stator 22 and the ball bearing preload screw 26. During operation, the thermal gap passively transfers heat from the rotor to the stator by virtue of lower temperatures and heat sinking capabilities of the stator.

The rotor 21 provides a relatively large rotary thermally conductive surface while the stator 22 acts as a relatively large thermally conductive stationary surface that thermally sinks heat from a resonator 16. Both rotor 21 and stator 22 are constructed from aluminum or other highly thermally conductive material, such as copper, cvd diamond, or graphite. The probe housing 12 has an internal temperature that is lower than that of the resonator 16. Internal to the resonator 16, the thermally conductive rotor 21 is positioned to optimize heat flow from the transducer array while not causing acoustic degradation from reflected ultrasonic waves.

The rotor/stator thermal cross sectional area may be increased or varied by employing a labyrinth or annular form where annular rings 30 machined into the rotor rotate in annular grooves 30A of the stator. The thermal coupling media 24 remains captive in the assembly by way of exposure to a geometry that inhibits fluid movement located at the potential located exit point. Exposure to a defined air gap will inhibit wicking as the total internal energy of the fluid will be insufficient to bridge the gap and drain the fluid reservoir.

The first and second ball bearings 28A, 28B are constructed as a preloaded pair designed to resist both thrust and radial loads. The preload may be applied by the use of the ball bearing preload screw 26 although other means may be employed. This arrangement is very stable when subjected to side loads as found on sensor array using flexible circuits, window interface, and drive gear. The rotor 21 is fabricated as a spur gear to be driven by a pinion to minimize rocking moments between the bearing and driven gear.

In this embodiment, the thermal coupling media 24 is a 0.0007" oil/grease layer. If either the rotor 21 or stator 22 is composed of graphite, such as in a graphite "wear in" design, the thermal gap may be reduced to zero.

Figure 2:
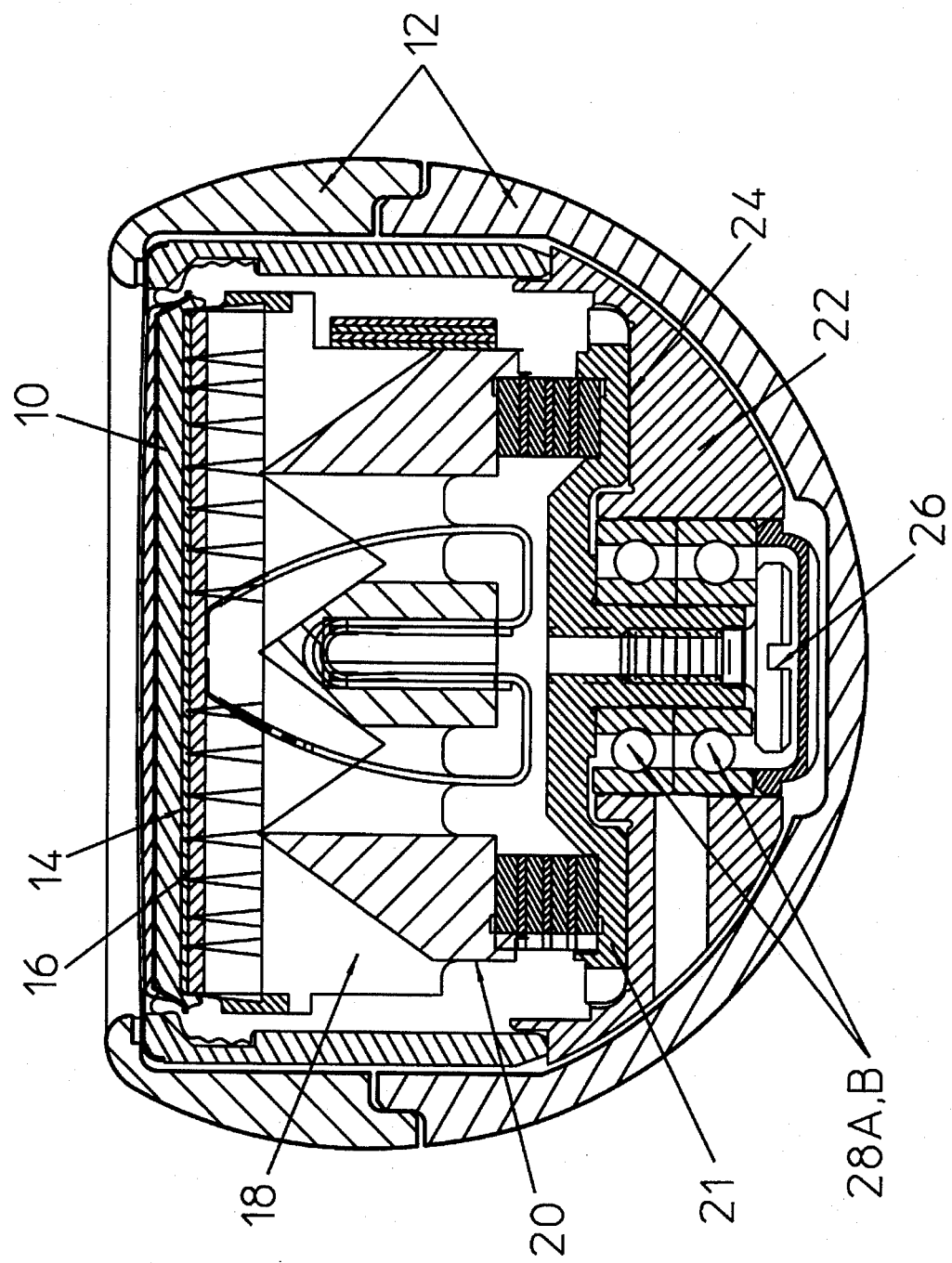
FIG. 2 illustrates an alternate embodiment for the cooling system.

FIG. 2 illustrates an alternate embodiment for the cooling system. The stator 22 is encompassed by the rotor 21. A thin oil layer is used as the thermal coupling media 24 at each rotor/stator interface to promote thermal sinking. The first and the second ball bearings 28A, 28B are a commercially available duplex pair, manufactured by New Hampshire Ball Bearing.

Figure 3:
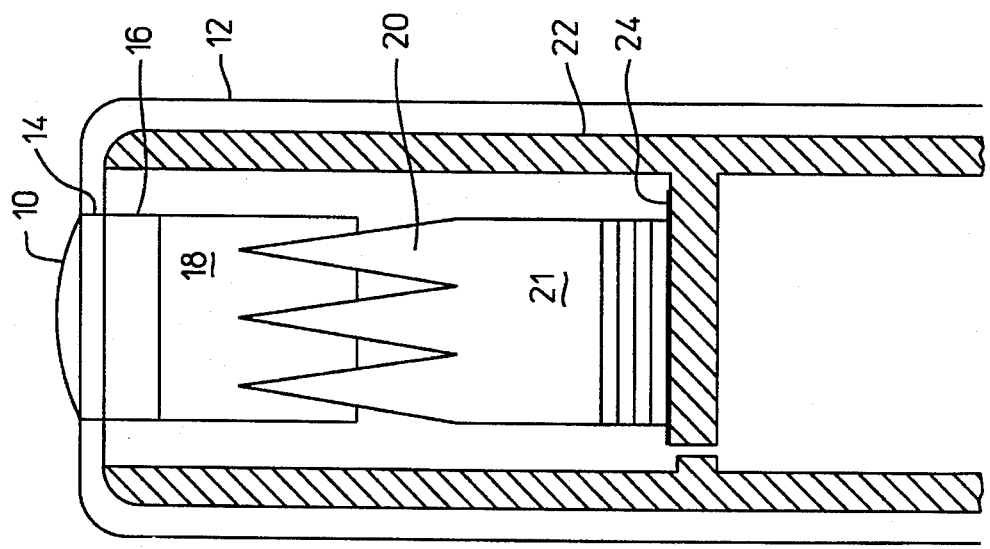
FIG. 3 illustrates another embodiment for the cooling system.

FIG. 3 illustrates another embodiment for the cooling system. In this embodiment, the resonator 16 is a stationary transducer array and the probe housing 12 serves as the fixed heat sink 22. The backing heat sink 20 does not rotate. Heat generated as a byproduct of the electrical to mechanical energy conversions is removed from the lens area of the transducer element through the dual heat sinking capability of the sensor to the handle case by virtue of lower handle temperatures.

For any of these embodiments, thermal performance may be enhanced by increasing the exposed areas of all heat transfer surfaces, changing to more highly conductive materials, such as copper or graphite, as well as reducing the internal temperature of the housing. The housing temperature may be maintained through active cooling, forced convection, or simply exposing more of the housing to ambient (which will be lower than the transducer array) conditions. Alternatively, the thin thermal coupling media may be oil, grease, graphite, or lead solder. Overall acoustic performance is enhanced by allowing more ultrasonic energy to be applied to the patient for a given probe surface temperature resulting in a larger received signal.

I claim:

1. A cooling system for cooling an ultrasound transducer assembly, the cooling system comprising:

an ultrasound transducer assembly;

a housing enclosing the ultrasound transducer assembly;

a backing heat sink of thermally conductive material, having a first and a second surface, the first surface positioned adjacent the ultrasound transducer assembly, the backing heat sink being rotatable;

a fixed heat sink of thermally conductive material, having a first and a second surface, the first surface positioned proximate to the backing heat sink;

a thermal coupling media, positioned between the backing and the fixed heat sinks, being operative to promote heat transfer;

a ball bearing preload screw, being operative to fasten the backing heat sink, the fixed heat sink, and the transducer element as an assembly such that the thermal coupling media is between the backing and fixed heat sinks;

a first ball bearing, positioned proximate to the second surface of the backing heat sink and the first surface of the fixed heat sink; and a second ball bearing, positioned proximate to the second surface of the fixed heat sink and the ball bearing preload screw.

2. A cooling system, as defined in claim 1, wherein:

the second surface of the backing heat sink including an annular ring;

the first surface of the fixed heat sink including an annular groove that is positioned over the annular ring; and the annular ring and groove are operative to house the thermal coupling media.

3. A cooling system, as defined in claim 1, wherein the thermal coupling media is a thin layer of oil.

4. A cooling system, as defined in claim 1, wherein the thermal coupling media is a graphite interface.

* * * * *